United States Patent [19]

Rosenlicht

[11] Patent Number: 5,312,254
[45] Date of Patent: May 17, 1994

[54] STERILE APPLICATION OF IMPLANTS IN BONE

[76] Inventor: Joel L. Rosenlicht, 59 Minnechaug Dr., Glastonbury, Conn. 06033

[21] Appl. No.: 37,773

[22] Filed: Mar. 26, 1993

[51] Int. Cl.⁵ .............................................. A61C 8/00
[52] U.S. Cl. .................................. 433/173; 433/174; 206/63.5
[58] Field of Search ............... 433/173, 174, 175, 176; 206/368, 369, 63.5

[56] References Cited

U.S. PATENT DOCUMENTS

| | | | |
|---|---|---|---|
| 4,856,648 | 8/1989 | Krueger | 206/63.5 |
| 4,856,994 | 8/1989 | Lazzara et al. | 433/173 |
| 4,955,811 | 9/1990 | Lazzara et al. | 433/173 |
| 5,062,800 | 11/1991 | Niznick | 433/173 |
| 5,100,323 | 3/1992 | Friedman et al. | 433/173 |
| 5,106,300 | 4/1992 | Voitik | 433/173 |
| 5,180,303 | 1/1993 | Hornburg et al. | 433/173 |

FOREIGN PATENT DOCUMENTS 2635455 2/1990 France .............................. 433/174

Primary Examiner—Cary E. O'Connor
Attorney, Agent, or Firm—M. P. Williams

[57] ABSTRACT

A sterile kit for inserting an implant to which a dental prosthesis may be fastened, includes an implant (14) having a combined insertion tool/transfer pin (50) secured thereto by a screw (16), with a carrier (52) mating with the combined insertion tool/transfer pin to start the implant into a hole prepared therefor. The method of use includes taking an impression as soon as the implant is secured in the bone, thereafter removing the combined insertion tool/transfer pin, inserting a healing screw (38), and forming the model of the mouth and ultimate prosthesis and abutments in a laboratory while the several month healing process takes place.

12 Claims, 2 Drawing Sheets

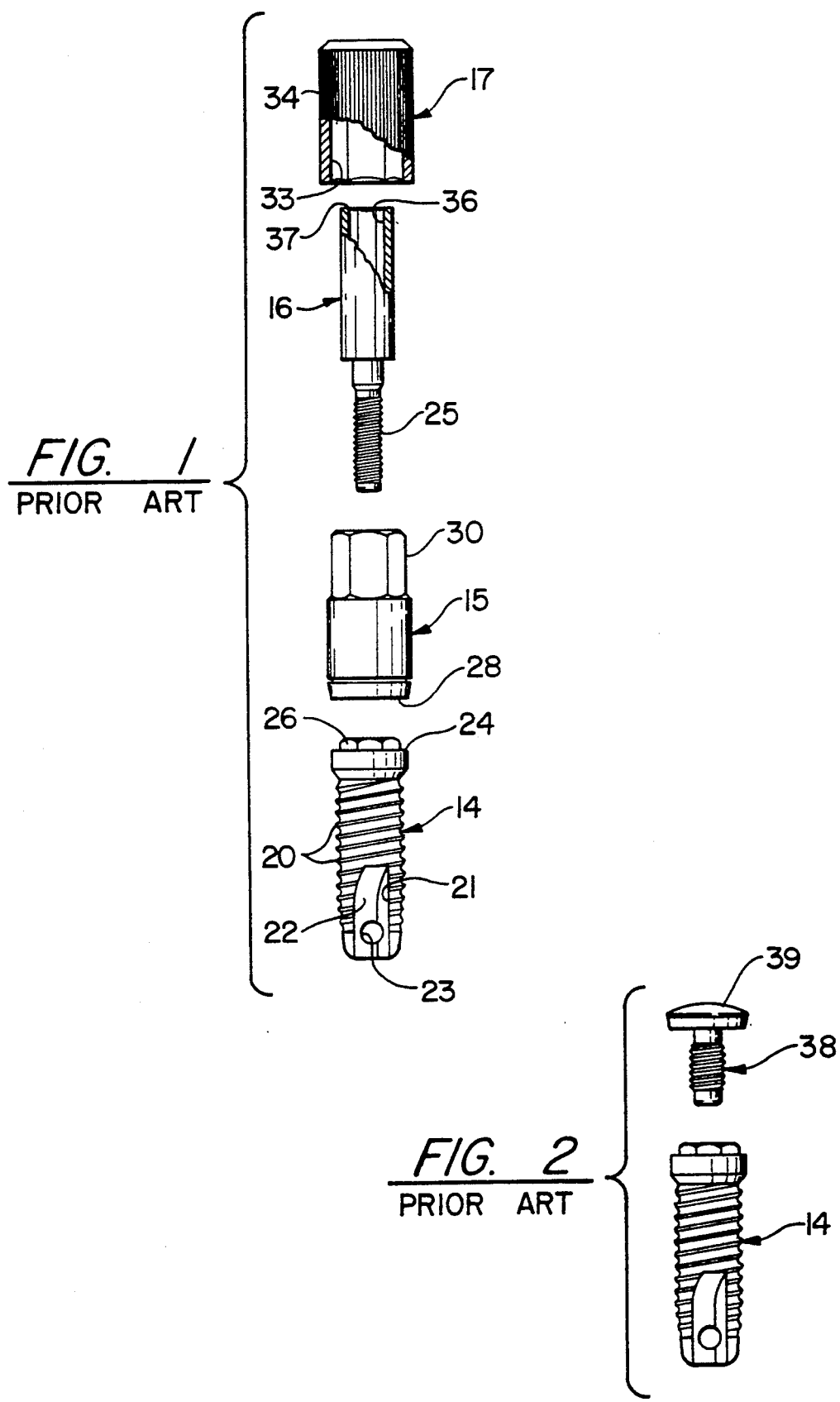

STERILE APPLICATION OF IMPLANTS IN BONE

TECHNICAL FIELD

This invention relates to improved, sterile insertion and utilization of implants in cone, such as dental implants.

BACKGROUND ART

In the 1930's, the first attempts to provide dental implants were unpredictable partially because of the materials which were used, and partially because of poor technique. The earliest implants were not capable of withstanding the loads provided thereto by chewing, the tongue and so forth.

During the 1960's and 1970's, the designs, materials and techniques utilized were radically altered and predictably acceptable results began to be achieved. The basic philosophy became to ensure that the implant was rigidly in place, with no capability for relative motion between it and the bony host. To ensure rigid securance of the implants, great care is taken to avoid any degradation of the immediately surrounding bone in preparing the site for the implant. Originally, the holes in the bones were tapped to provide an identical fit to screw threads on the implants; and in order to avoid excessive heat, low speed, high torque drills were used with cooling fluids. Implants are made of pure titanium or titanium alloys which are compatible with bone, fixtures, tools, and the ultimate prosthesis, as well as being innocuous in use over time. A sterile field was attempted to be maintained at all times.

Since then, many more improvements have been made in the materials, the parts, and the techniques. By way of example, a procedure which is widely practiced currently, illustrated in FIG. 1, utilizes a kit, contained in a sterile package, that includes a self-tapping implant 14, an insertion tool 15, held to the implant by a screw 16, and a carrier 17. The implant has threads 20, a self-tapping cutting edge 21, a recess 22, formed with the edge 21, which may have a hole 23 leading to a similar recess on the opposite side. The recess provides a place for the bone debris that forms from cutting the threads, thereby avoiding packing of the debris between the implant and the surrounding bone. The center of an outer end 24 of the implant is hollow and threaded (not shown) to receive the threads 25 of the screw 16. The outer end 24 also has a shallow hexagonal land 26 thereon for aligning the ultimate prosthesis (or abutment) therewith and for screwing the implant into the hole drilled into the bone. The land 26 is engaged by a hexagonal socket 28 formed in the insertion tool 15. The upper third (or so) of the insertion tool 16 has a hexagonal surface 30 which is engaged, initially by a hexagonal socket 33 formed in the carrier 17; the carrier may have serrations 34, or other features, to assist in handling it.

As shipped in a sterile bottle or other sterile package, the tool 15 is tightly secured over the land 26 by the screw 16, and the carrier 17 surrounds the hex surface 30 of the tool. The carrier typically forms the stopper of an interior bottle in a double sterile package. The implant may thus be hand started into the hole in the bone by means of the carrier. The carrier can then be shaken loose and removed. A socket wrench is then used to seat the implant subgingivally into the bone. Thus the process of securing the implant to the bone is readily achieved, with the sterility of all but the wrench ensured by packaging.

Once the implant 14 is properly secured in its final position, a hexagonal wrench is used to engage a hexagonal socket 36 formed in the outer end 37 of the screw, the screw 16 is backed out of the implant, and the insertion tool 15 is removed. Next, a healing screw 38 (FIG. 2) is threaded tightly into the implant to keep the outer end 24, the land 26 and the internal threads of the implant all clean and clear, as the gum tissue is allowed to heal over the healing screw. The healing screw 38 has a hex socket in its head 39 (not shown, similar to that of the screw 16) to permit rotating it with a hex wrench. The head 39 has an annular void to fit over, but not engage, the hexagonal land 26 on the implant 14.

This procedure requires that, after the implant is secured into the bone, the gum tissue covering the implant and healing screw thoroughly heal. For implants in the mandible, healing requires about three months; in the maxilla, about six months.

After healing, the gum is reopened, the healing screw 38 is removed, and an impression transfer pin 40 (FIG. 3) is secured to the implant 15 by a screw 41. The screw 41 may be rotated with a friction drive wrench. The transfer pin 40 is fit tightly to the implant 15 and x-rayed to ensure that it is tight and well mated, with no voids. Then, an impression is taken of the patient's mouth with the transfer pin in place. After the impression is completed, the screw and transfer pin are removed and a healing abutment (not shown) is threaded into the implant; the healing abutment typically extends above the gum line, so that the gum tissue can reheal, leaving an orifice open to the implant for later insertion of a suitable abutment which mounts the prosthesis.

While the second healing takes place, a laboratory prepares a working model of the mouth from the impression, utilizing the transfer pins, imbedded in the impression, to seat implant analogs (or dies) to which the prosthesis may be secured on the working model. Then the lab prepares the prosthesis, with the abutments which will be utilized for anchoring the prosthesis on the implants, secured to the implant analogs.

This process is long and cumbersome and has less than complete predictability, is traumatic for the patient, and difficult. In addition, maintaining sterility while manipulating all the small parts involved is a chore in itself. Furthermore, it is not uncommon for some of the small pieces to actually become lost (even down the throat of the patient). Visibility of the implant may be limited by blood and tissue.

In the process described above, the transfer pin is typically not provided in the sterile kit. As a consequence, there is a general practice of using the transfer pins over and over again. The transfer pins can become nicked and may have bits of material adherent thereto which together provide irregularities in the surface that impede both the seating of the transfer pin securely to the implant, without voids, prior to making the impression, as well as interfering with a faithful return to the impression when the construction is commenced. Furthermore, the seating of a transfer pin on an implant in a freshly prepared site is very likely to be less than perfect, with tissue or other debris lodging between the transfer pin and the implant; it is very unlikely that a debris-impeded fit would be replicated upon mounting an abutment for the prosthesis to the implant at the conclusion of the procedure.

In some cases, single stage implants, with abutments integrally formed thereon, have been used in a procedure which takes the impression on the mouth immediately after installing the implants. This procedure has not had general acceptance because it must be executed with extreme skill and without any significant anatomical contra indications or procedural mishaps. The temporization (protection) of the abutments through the tissue is also difficult. In contrast, the two stage process (hereinbefore) permits compensating for any incorrect angles or other misplacements of the implants. Furthermore, the abutment ends of the integrally formed implants are protected from tongue and chewing pressures for months, to avoid faulty healing. This requires easily adapting an existing denture or providing a temporary prosthesis, to cover the implants during healing.

DISCLOSURE OF INVENTION

Objects of the invention include mounting a bone implant, such as in a patient's mouth for prosthodontic restoration, in a manner requiring a minimal handling of parts, reducing patient visits, with improved results, and significantly reducing the elapsed time from the beginning to the conclusion of the prosthodontic procedure.

This invention is predicated in part on the discovery that taking an impression at the first sitting of the patient, immediately following the insertion of the implants into the bone, has no significant pathological morbidity or other detrimental effects. The invention is also predicated on the discovery that the location of implants, utilized in a two-stage process, remain essentially constant so that initial impressions are as accurate as impressions made following a several month healing period.

According to the present invention, a sterile package includes an implant having secured thereto a transfer pin which also serves as an insertion tool, the package including a carrier which has a unique interior wall surface engaging the combination insertion tool/transfer pin, so that the implant may be started into the bone in a sterile manner, using the aforementioned components shipped as a sterile set. The invention includes a method in which an impression is taken as soon as the carrier is removed from the combined insertion tool/transfer pin, (unless contra-indicated) after which the transfer pin is removed and a healing screw is inserted to the outer end of the implant in order to keep it clean for ultimate mating with an abutment which will mount the prosthesis.

The invention, by taking the impression immediately, allows the laboratory work—forming of the model of the mouth and the ultimate prosthesis and/or abutment structure—to be performed while the initial, several-month healing takes place. The invention avoids having to enter the gum tissue more than twice, since the second invasion is to remove the healing screw and mount the ultimate abutments and/or prosthesis (in most cases). One great advantage of the present invention is that it avoids the necessity for handling a transfer pin and concomitant screw at a second sitting, after healing has taken place. Thus, fewer steps are required, as fewer parts are handled. This significantly reduces the risk of infection as well as significantly reducing the risk of loosing small parts—possibly in a patient. Another great advantage of the present invention is that the transfer pin is always firmly and tightly secured to the implant at the factory, under ideal conditions, rather than being attached to the implant in the surgical field. A concomitant advantage is that providing a new insertion pin for each implant avoids the possibility of poor fit to the implant due to scratches in the mating surface of the transfer pin or inter-lodging debris. The invention also eliminates the use of two parts: the insertion tool and the screw used to hold the original transfer pin.

Other objects, features and advantages of the present invention will become more apparent in the light of the following detailed description of exemplary embodiments thereof, as illustrated in the accompanying drawing.

BRIEF DESCRIPTION OF THE DRAWINGS

FIG. 1 is an exploded, partially sectioned side elevation view of a sterile set comprising an implant, an insertion tool, a screw and a carrier known to the prior art.

FIG. 2 is an exploded side elevation view of a healing screw and an implant, known to the prior art.

BEST MODE FOR CARRYING OUT THE INVENTION

Figure 3:
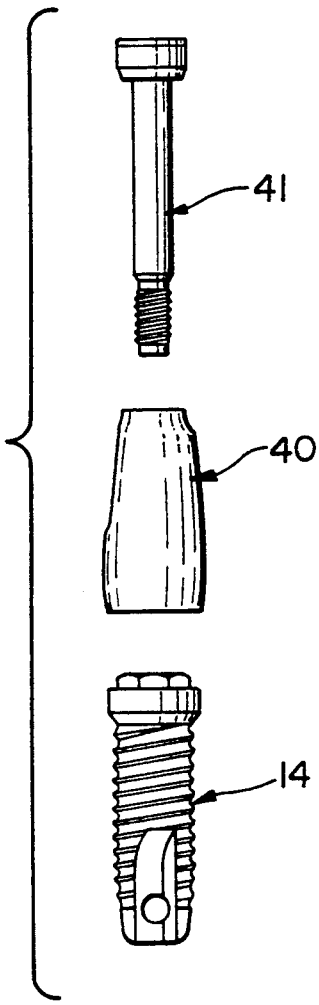
FIG. 3 is an exploded side elevation view of an implant and a transfer pin together with a screw for securing the transfer pin to the implant, in accordance with the prior art.
Figure 4:
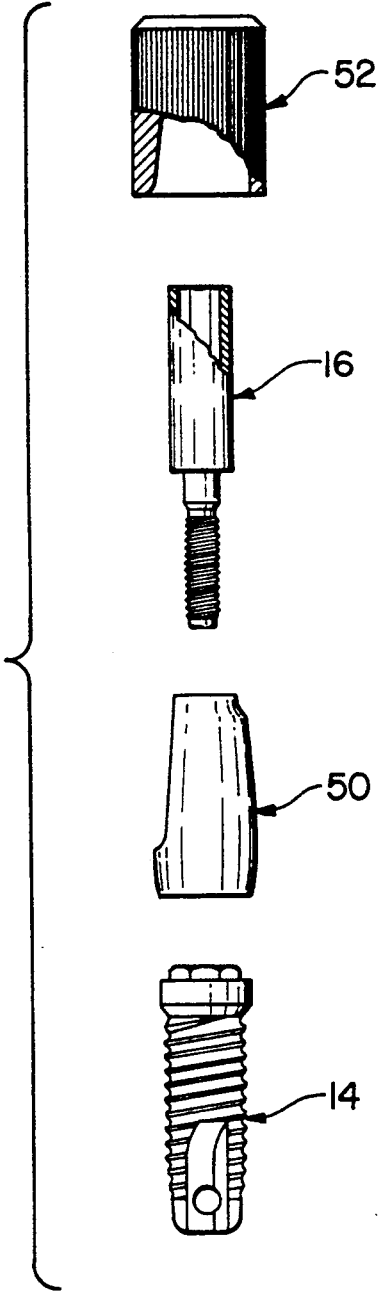
FIG. 4 is an exploded, partially sectioned side elevation view of a sterile set comprising an implant, a combined insertion tool/transfer pin, a screw for securing the combined insertion tool/transfer pin to the implant, and a carrier, in accordance with the present invention.

Referring now to FIG. 4, a combined insertion tool/transfer pin 50 may take a variety of forms, the one illustrated herein is a severely timed transfer pin. As is true of the prior art transfer pin 40, the combined insertion tool/transfer pin 50 is hollow all the way through, so as to permit it to be fastened to the implant 14 by means of the screw 16, both of which may be the same as in the prior art. According to the invention, the implant 14, combined pin 50 and screw 16 are assembled with the screw 16 passing through the combined pin 50 and securing it tightly to the implant 14, with a carrier 52 surrounding the screw 16 and engaging the flat land surface of the combined pin 50 so as to permit transfer of rotary torque thereto sufficiently to start the implant 14 into the hole prepared therefor. The parts so assembled are shipped in a sterile container as known in the art, which may comprise a small plastic or glass bottle within a larger bottle, or otherwise, as suits any implementation of the present invention.

According to the invention, as soon as the implant 14 has been threaded part way into the hole prepared for it, the carrier 52 is shaken loose of the combined pin 50 and the screw 16 and removed from the mouth. A socket wrench, with a socket surface shaped to engage the combined pin 50 and/or a screw, is used to drive the implant 14 into its intended position. Then an impression of the mouth is made with the combined pin 50 serving as the transfer pin for the impression. When the impression is complete, a hex wrench is used to unthread the screw 16 from the implant 14, so that the combined pin 50 can be removed from the mouth. Then, as is true in the prior art, a healing screw 38 is fastened into the implant 14 (FIG. 2).

Healing is allowed to take place for several months, as in the prior art. However, in accordance with the invention, since the impression has already been made, the lab work may be done while healing takes place. This, therefore, saves significantly in the total elapsed time required for a procedure. When the prosthesis is ready for installation and healing is complete, an incision is made into the gum, the healing screw 38 is removed, and the prosthesis and suitable abutment are secured to the implant 15, and the gum allowed to heal finally. This is only the second invasion, rather than the third invasion required in the prior art. The invention also avoids the necessity for the use and handling of a second healing screw or healing abutment during the time between taking the impression and preparing the prosthesis. While it is possible that certain of the parts may cost more than the parts used heretofore, less parts are used. And while a wrench suitable for turning the combined insertion tool/transfer pin 50 may seem to be extremely complex, it is in fact quite similar to a well-known fixed abutment tool already available in the art.

Elimination of one or more patient sittings, reducing all of the extraneous lab time because it falls within the healing time, reducing the number of handlings of parts and the number of parts used, and ensuring that the transfer pin is perfectly secured to the implant before the impression is made, are all significant advantages of the invention.

The examples herein are exemplary merely. There are myriad prosthodontic parts and variations in shapes and techniques known in the art. For instance, a self-tapping, threaded implant with a hexagonal land for transferring torque thereto is used as the example herein. However, press-fit straight or cylinder implants which are tapped into the hole, as well as blade implants which are tapped into a prepared groove, may be used in practicing the invention, the carrier in that case serving to hold the implant while it is transferred to the hole or the groove and to conduct tapping from above the gum line to the implant as it is seated subgingivally. The implant surfaces may be sandblasted or may have any of a variety of coatings known to the art. Although the description herein may suggest use for a single reconstruction (a cap), the invention may be used with two or several implants. The invention has an additional advantage that when several implants are being placed, such as may ultimately support a fixed, fixed-removable or other denture, the complete insertion of the first implant while the combined pin 50 remains secured thereto by the screw 16, provides a guide to assist the practitioner in preparing parallel holes at the sites of the additional implants, by visual benchmarking against the combined pin 50. Although the transfer pin 40 and combined pin 50 disclosed herein have smooth surfaces, a combined pin in accordance with the present invention may have lateral grooves therein (which tend to snap the transfer pin into the elastic impression), or other transfer pin shapes, as are known in the art.

The invention has been shown with a hex land and socket relationship between the implant and the combined pin 50. This allows assuring reorientation of the transfer pin correctly with respect to the implant. However, it is known to use slots, clover leafs and other shapes to assure registration, all of which are within the scope of this invention. Further, in some cases the combined pin 50 may comprise a temporary or permanent abutment utilized to make the impression for the model of the mouth, after which it could remain in place during healing (as a healing abutment or to anchor a temporary prosthesis), and/or used as the ultimate abutment. In that situation, an abutment analog may be used in constructing the prosthesis to the model of the mouth. In fact, the invention is not limited to prosthodontia, but may be used in securing any form of artificial body part to bone, specifically including eyes, ears and noses and subcutaneous structures for supporting living or non-living reconstructions thereof.

It is irrelevant which type of implant is used, and it is irrelevant which sort of a transfer pin or sterile set may be used. What is relevant in the invention is that the transfer pin be utilized as an insertion tool so as to permit taking an impression immediately after inserting the implant, the field remaining sterile because of the kit according to the invention, which does not require exchanging an insertion tool with a transfer pin.

One of the great advantages of the invention is having the laboratory work commence immediately upon inserting the implants into the bone, due to the presence of the combined pin 50 in the sterile kit. However, the practitioner must, as always, make clinical decisions about the appropriateness of any stage of a procedure. Should the practitioner decide that the impressions should not be made immediately upon placement of the implants as described hereinbefore, then the taking of the impression can be delayed. An example might be where there is unusual trauma from site preparation.

Thus, although the invention has been shown and described with respect to exemplary embodiments thereof, it should be understood by those skilled in the art that the foregoing and various other changes, omissions and additions may be made therein and thereto, without departing from the spirit and scope of the invention.

I claim:

1. A method of providing an implant secured to a reconstruction site in a cavity in the bone of a patient, to which a prosthesis may be fastened, comprising:

providing a sterile kit including an implant, an impression transfer pin secured to the implant and capable of use as an insertion tool for inserting the implant into a cavity provided therefor in the bone of a patient, a screw retaining the transfer pin to the implant, and a carrier for handling the aforementioned parts while beginning the process of inserting the implant into the bone;

using the carrier, starting the implant into the cavity;

dislodging the carrier from the other ones of said parts and removing the carrier from said site;

inserting the implant into its intended position in the bone, selectively utilizing an additional tool as necessary;

taking an impression of the site so as to permit preparing a model of the site;

loosening said screw and removing said screw and said pin from said implant and from said site; and fastening a healing abutment to said implant.

2. A method according to claim 1 wherein said site is in a mouth and said prosthesis includes a replacement tooth.

3. A method according to claim 1 including, following said fastening step: allowing the site to heal while concomitantly, using said impression, preparing a prosthesis to be fastened to the implant; and when healing is complete, forming an incision at and removing said healing abutment, and fastening the prosthesis to the implant.

4. A method of providing an implant secured in a hole in the maxilla or mandibular bone of a patient, to which a dental prosthesis may be fastened, comprising:

providing a sterile kit including an implant, an impression transfer pin secured to the implant and capable of use as an insertion tool for inserting the implant into a hole provided therefor in the bone of a patient, a screw retaining the transfer pin to the implant, and a carrier for holding the aforementioned parts while beginning the process of inserting the implant into the bone;

using the carrier, starting the implant into the hole;

dislodging the carrier from the other ones of said parts and removing the carrier from the mouth;

inserting the implant into its intended position in the bone, selectively utilizing an additional tool as necessary;

taking an impression of the mouth so as to permit preparing a model of the mouth;

loosening said screw and removing said screw and said transfer pin from said implant and from the mouth;

fastening a healing abutment into said implant;

thereafter allowing the gum to heal for at least one month while concomitantly, using said impression, preparing a prosthesis to be fastened to the implant; and when healing is complete, forming an incision at and removing said healing abutment, and fastening the prosthesis to the implant.

5. A method according to claim 4 wherein said step of fastening a healing abutment comprises inserting a healing screw into said implant.

6. An implant kit, comprising:
a sterile package, said sterile package including:
a screw;
an implant;
a transfer pin shaped so as to be able to function as an insertion tool in inserting said implant into a cavity prepared therefor in the bone of the patient, said transfer pin being secured to said implant by means of said screw; and
a carrier disposed to engage said transfer pin so that manipulation of said carrier may start said implant into the cavity prepared therefor.

7. An implant kit according to claim 6 wherein said implant is threaded, and said carrier engages said transfer pin so that rotation of said carrier imparts rotation to said implant so as to threadably engage the cavity.

8. An implant kit according to claim 7 wherein said implant is self-tapping.

9. An implant kit according to claim 6 wherein said implant has a hexagonal shape at the end thereof which engages said transfer pin, and said transfer pin has a complimentary hexagonal shape in the end thereof which engages said implant.

10. An implant kit according to claim 9 wherein said implant has a hexagonal land on the end thereof that engages said transfer pin, and said transfer pin has a hexagonal socket formed in the end thereof that engages said implant.

11. An implant kit according to claim 6 wherein said implant is particularly adapted for utilization in securing a dental prosthesis in the mouth of a patient.

12. An implant kit according to claim 6 wherein said transfer pin is particularly adapted for utilization in orienting a prosthesis to a model of the mouth of a patient made from an impression taken with said transfer pin secured to said implant.

* * * * *